US009849260B2

(12) United States Patent
Black et al.

(10) Patent No.: US 9,849,260 B2
(45) Date of Patent: Dec. 26, 2017

(54) ADHESIVE DEVICES AND METHODS FOR IMPROVING BREATHING AND/OR SLEEP USING SUCH DEVICES

(71) Applicants: Jed Eric Black, Palo Alto, CA (US); Stephen A. Leeflang, Sunnyvale, CA (US); Christian S. Eversull, Palo Alto, CA (US)

(72) Inventors: Jed Eric Black, Palo Alto, CA (US); Stephen A. Leeflang, Sunnyvale, CA (US); Christian S. Eversull, Palo Alto, CA (US)

( * ) Notice: Subject to any disclaimer, the term of this patent is extended or adjusted under 35 U.S.C. 154(b) by 314 days.

(21) Appl. No.: 14/200,010

(22) Filed: Mar. 6, 2014

(65) Prior Publication Data

US 2014/0251335 A1 Sep. 11, 2014

Related U.S. Application Data

(60) Provisional application No. 61/773,711, filed on Mar. 6, 2013, provisional application No. 61/816,380, filed on Apr. 26, 2013.

(51) Int. Cl.
| | |
|---|---|
| *A61B 18/08* | (2006.01) |
| *A61M 16/06* | (2006.01) |
| *A61M 16/20* | (2006.01) |
| *A61F 5/56* | (2006.01) |

(52) U.S. Cl.
CPC .......... *A61M 16/0616* (2014.02); *A61F 5/56* (2013.01); *A61M 16/0688* (2014.02); *A61M 16/208* (2013.01)

(58) Field of Classification Search
CPC ..... A61F 5/56; A61M 16/0048; A61M 16/20; A61M 16/208; A61M 16/0616; A61M 16/0688; A61M 16/0488; A61M 16/049
USPC .................. 128/202.28, 2–2.29, 203.11
See application file for complete search history.

(56) References Cited

U.S. PATENT DOCUMENTS

| | | | | | |
|---|---|---|---|---|---|
| 746,869 | A | * | 12/1903 | Moulton .................. | A61F 5/566 128/848 |
| 1,354,652 | A | * | 10/1920 | Jefferies ..................... | A61F 5/56 128/206.25 |
| 1,629,892 | A | * | 5/1927 | Storms ....................... | A61F 5/56 128/848 |
| 1,775,718 | A | * | 9/1930 | Garvey ..................... | A61F 5/56 128/848 |

(Continued)

*Primary Examiner* — Bradley Philips
*Assistant Examiner* — Victoria Leszczak
(74) *Attorney, Agent, or Firm* — William A. English; Vista IP Law Group LLP

(57) ABSTRACT

Devices and methods are provided for inhibiting mouth breathing and/or improving nasal breathing, e.g., for PAP users or users with other sleeping problems. In an exemplary embodiment, an adhesive device is provided that includes an elongate membrane comprising first and second ends and side edges extending between the first and second ends, a first surface comprising an adhesive layer. The adhesive layer may be a low tack adhesive that is adherent to skin, yet is also easily removable without leaving significant residue. Optionally, the device may include one or more valves to provide one-way flow across the membrane, one or more weakened regions in the membrane, and/or one or more tabs to facilitate removal of the membrane from over a user's mouth.

9 Claims, 4 Drawing Sheets

(56) References Cited

U.S. PATENT DOCUMENTS

| | | | | |
|---|---|---|---|---|
| 4,817,636 | A * | 4/1989 | Woods | A61F 5/56 128/848 |
| 5,560,354 | A * | 10/1996 | Berthon-Jones | A61M 16/0616 128/204.18 |
| 6,076,526 | A * | 6/2000 | Abdelmessih | A61F 5/56 128/848 |
| 6,089,232 | A * | 7/2000 | Portnoy | A61F 5/56 128/848 |
| 6,148,820 | A * | 11/2000 | Herrin | A61F 5/56 128/848 |
| 2003/0149387 | A1* | 8/2003 | Barakat | A61F 5/56 602/45 |
| 2005/0178392 | A1* | 8/2005 | Tinsley | A61F 5/56 128/848 |
| 2006/0070629 | A1* | 4/2006 | Haddix | A61F 5/56 128/848 |
| 2007/0283962 | A1* | 12/2007 | Doshi | A62B 23/06 128/206.15 |
| 2008/0041397 | A1* | 2/2008 | Hirs | A61F 5/56 128/848 |
| 2008/0053459 | A1* | 3/2008 | Silker | A61F 5/566 128/848 |
| 2009/0050144 | A1* | 2/2009 | Pierce | A61F 5/56 128/200.24 |
| 2009/0114229 | A1* | 5/2009 | Frater | A61M 16/06 128/206.24 |
| 2012/0244103 | A1* | 9/2012 | Davis | A61F 5/56 424/78.02 |
| 2014/0000632 | A1* | 1/2014 | Chen | A61F 5/56 128/848 |

\* cited by examiner

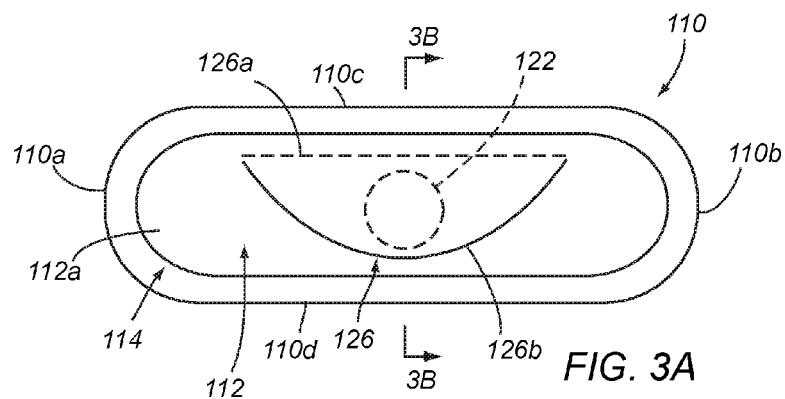
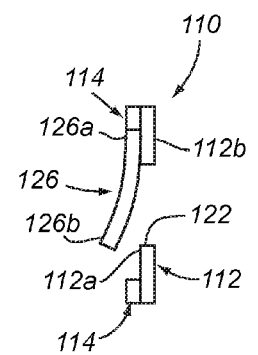
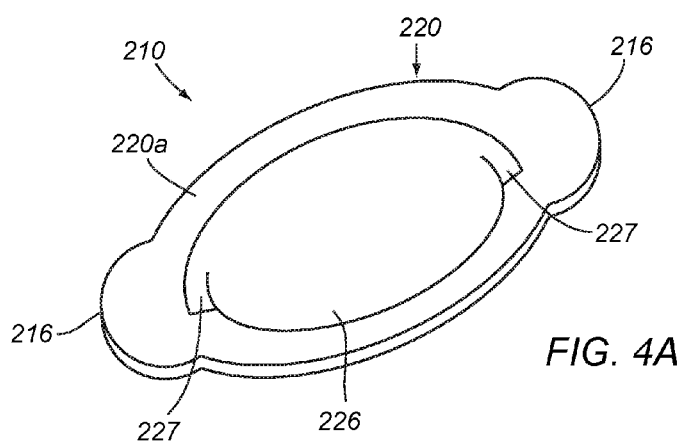
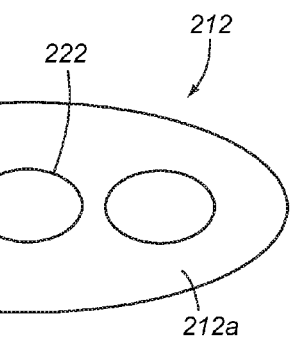
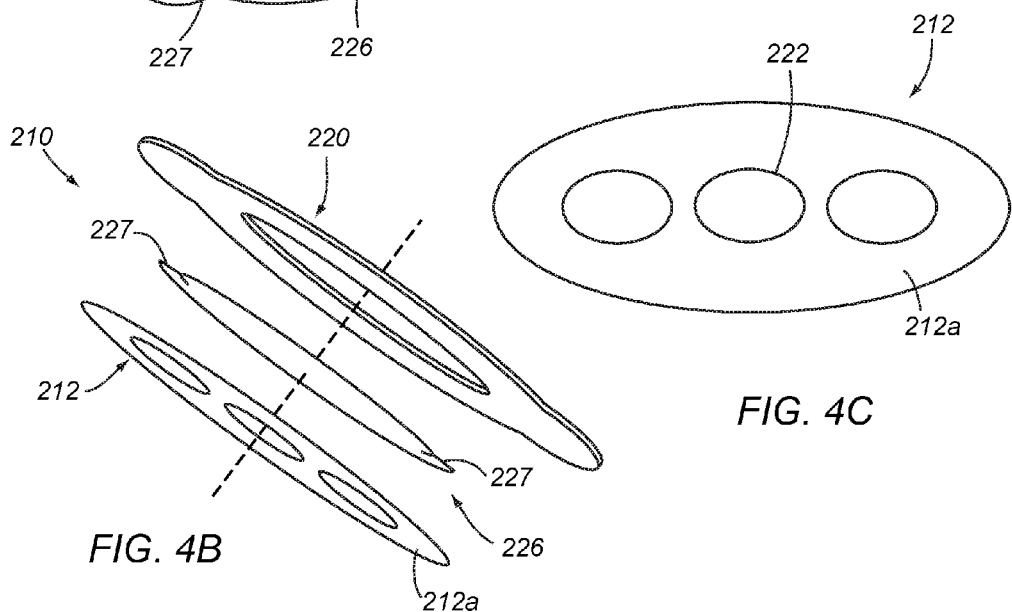

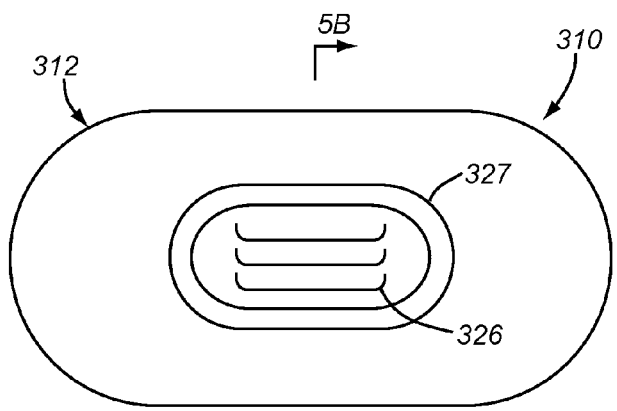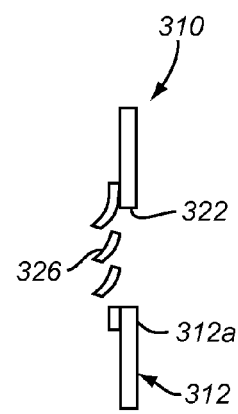
FIG. 5A
FIG. 5B
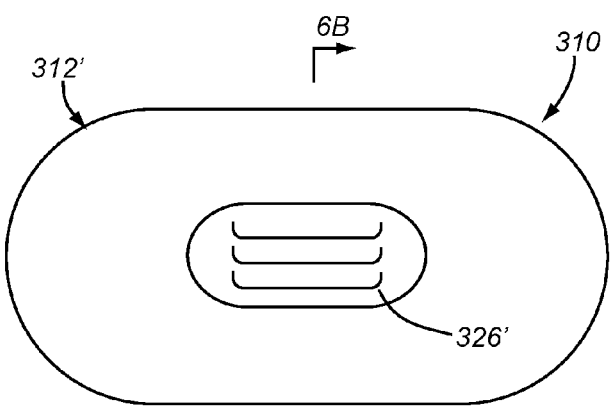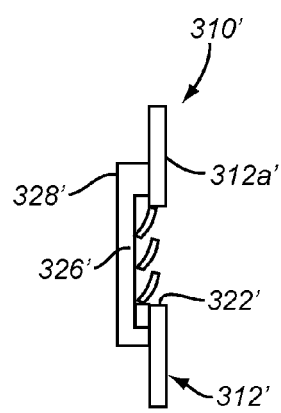
FIG. 6A
FIG. 6B

ADHESIVE DEVICES AND METHODS FOR IMPROVING BREATHING AND/OR SLEEP USING SUCH DEVICES This application claims benefit of U.S. provisional application Ser. Nos. 61/773,711, filed Mar. 6, 2013, and 61/816,380, filed Apr. 26, 2013, the entire disclosures of which are expressly incorporated by reference herein.

FIELD OF THE INVENTION

The present invention relates generally to devices and methods for improving breathing and/or sleep, e.g., to adhesive devices for application over a user's mouth to hold the lips, jaw, and/or mouth closed to facilitate nasal breathing, e.g., during use of a positive airway pressure (PAP) or oral pressure therapy (OPT, e.g., Winx®) device and/or to reduce snoring or other breathing problems while sleeping, and/or to improve sleep-related dry mouth and dry-mouth-related oral and dental disease.

BACKGROUND

For a number of reasons and in a variety of conditions, mouth breathing causes or exacerbates snoring, sleep apnea, and/or dry mouth. For example, during use of nasal PAP devices for sleep apnea, positive pressure may be applied to the nose via a nasal mask. However, an open mouth allows the applied positive pressure to simply escape through the mouth rather than open the airway, thus negating the therapeutic value of PAP. Further, even outside of PAP use, breathing through the mouth or having an open mouth may increase snoring, apneas, dry mouth, and the like compared to natural nasal breathing.

A range of products have been proposed to address these problems. For example, PAP full face masks may be used to cover both the nose and the mouth of a user. However, such masks may involve challenges such as sealing and comfort. In addition, chin straps may be used in an attempt to hold up the chin up and keep the mouth closed.

In addition, during normal sleep, jaw opening and/or retraction may encourage collapse of the posterior pharynx and increase airway obstruction. Mouth breathing during sleep also dries the airway. Both of these conditions may encourage snoring. Dry mouth can also cause or exacerbate mouth and gum tissue deterioration and disease and/or tooth decay and disease.

Accordingly, devices and methods for improving breathing, sleep, and/or mouth dryness would be useful.

SUMMARY

The present invention is directed generally to devices and methods for sealing the lips and/or mouth, maintaining jaw position, encouraging natural nasal breathing and/or otherwise improving breathing and/or sleep. More particularly, the present invention is directed to adhesive devices for application over a user's mouth to hold the mouth closed to facilitate normal nasal breathing, e.g., during use of a PAP device, to encourage normal nasal breathing, reduce snoring or other breathing problems while sleeping, and/or to reduce sleep-related dry mouth, and to methods for using such devices.

Lips have the natural ability to seal and are quite elastic. Even when the jaw drops and/or opens, the lips may stay closed if held closed. However, when the jaw is open and the individual is asleep, the lips tend to relax and the mouth may open, compromising use of PAP devices and/or increasing snoring and/or other breathing problems, e.g. due to mouth breathing. The force required to keep the lips closed even with the jaw open is minimal, especially compared to the force required to keep the chin up and jaw closed in the typical snorer or sleep apnea sufferer. Thus, a novel and helpful device may generally keep the lips closed while providing a number of related features to ensure safety and/or comfort.

In accordance with one embodiment, a device is provided for improving breathing and/or inhibiting mouth breathing that includes a mouth cover comprising an annular member defining a central open region therethrough and including a first surface comprising adhesive thereon for detachably attaching the mouth cover to skin of a user surrounding the user's mouth; and a lip closing element comprising an elastic membrane attached to a second surface of the mouth cover opposite the first surface and extending across the central open region and including one or more openings therethrough.

Optionally, the device may include one or more valves, e.g., a one-way valve attached to the mouth cover, for selectively sealing the one or more openings. For example, when a positive pressure within a user's mouth is generated between the first and second surfaces, the one or more valves may seal the one or more openings, while, when a user inhales to generate a negative pressure between the first and second surfaces, the one or more valves may open the one or more openings.

In accordance with another embodiment, a device for inhibiting mouth breathing is provided that includes an elongate membrane comprising first and second rounded ends and side edges extending between the first and second ends, the elongate member including a first surface comprising an adhesive layer, the adhesive layer comprising a low tack adhesive that is adherent to skin, yet is also easily removable without leaving significant residue. Optionally, the device may include one or more weakened regions in the membrane, the one or more weakened regions configured to separate and allow breathing through the user's mouth when the user forcibly separates the user's lips and/or inhales or exhales above a predetermined pressure threshold. In addition or alternatively, the device may include one or more tabs extending from the membrane, each tab having non-adhesive surfaces and configured to facilitate removal of the membrane from over a user's mouth.

In accordance with still another embodiment, a device is provided for inhibiting mouth breathing that includes a membrane comprising first and second ends and side edges extending between the first and second ends; an adhesive layer on a first surface of the membrane adherent to skin to allow the membrane to be detachably attached over a user's mouth; and one or more weakened regions in the membrane configured to separate and allow breathing through the user's mouth when the user inhales or exhales to generate a pressure across the membrane greater than a predetermined pressure threshold and/or when the user forcibly separates the user's lips.

In accordance with yet another embodiment, a device is provided for inhibiting mouth breathing that includes a membrane comprising first and second ends and side edges extending between the first and second ends; an adhesive layer on a first surface of the membrane adherent to skin to allow the membrane to be detachably attached over a user's mouth; and a tab extending from the membrane comprising non-adhesive surfaces and configured to facilitate removal of the membrane from over a user's mouth.

In accordance with another embodiment, a method is provided for improving breathing of a PAP user that includes placing a nasal mask for a PAP device over a user's nose; applying a membrane over the user's mouth to prevent breathing through the user's mouth; and activating the PAP device.

In accordance with still another embodiment, a method is provided for improving nasal breathing that includes applying a membrane over a user's mouth with the user's lips pressed together; and sleeping with the membrane over the user's mouth to inhibit breathing through the user's mouth.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary devices shown in the drawings are not necessarily drawn to scale, with emphasis instead being placed on illustrating the various aspects and features of the illustrated embodiments.

FIG. 3A is a front view of another embodiment of an adhesive device.

FIG. 3B is a cross-sectional view of the adhesive device of FIG. 3A taken along line 3B-3B.

FIGS. 4A and 4B are perspective and exploded views, respectively, of another embodiment of an adhesive device.

FIG. 4C is a front view of a lip closing element that may be included in the adhesive device of FIGS. 4A and 4B.

FIGS. 5A and 6A are front views of additional embodiments of adhesive devices.

FIGS. 5B and 6B are cross-sectional views of the adhesive devices of FIGS. 5A and 6A taken along lines 5B-5B and 6B-6B, respectively.

DETAILED DESCRIPTION OF THE EXEMPLARY EMBODIMENTS

Figure 1A:
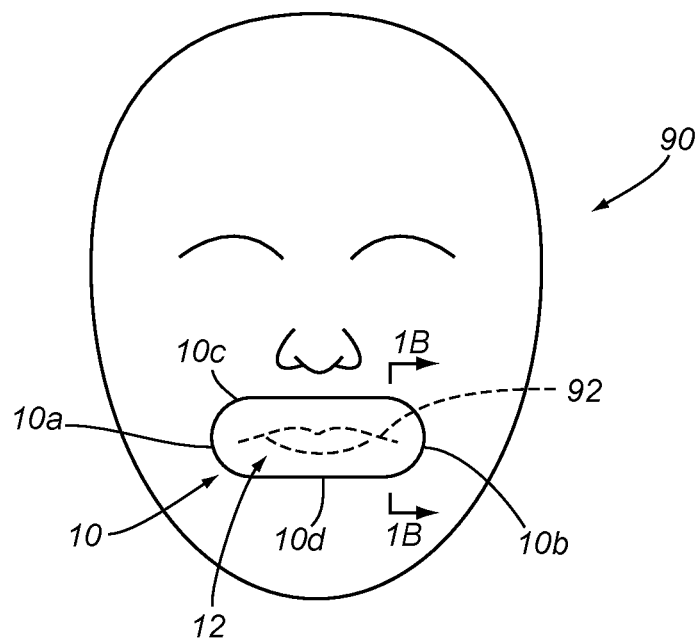
FIG. 1A is a front view of an exemplary embodiment of an adhesive device applied over a user's mouth.
Figure 1B:
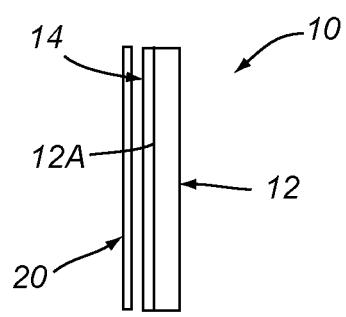
FIG. 1B is a cross-sectional side view of the adhesive device of FIG. 1A taken along line 1B-1B.

Turning to the drawings, FIGS. 1A and 1B show an exemplary embodiment of an adhesive device 10 that generally includes a flexible membrane 12 sized for application over a user's mouth 92 and an adhesive layer 14. Optionally, the adhesive device 10 may also include a removable cover sheet 20, e.g., as shown in FIG. 1B, which may be provided over the adhesive layer 14 to prevent exposure before use.

The membrane 12 may be formed from nonporous material, e.g., to substantially seal the user's mouth to prevent air from passing therethrough. Alternatively, the membrane 12 may simply be configured to maintain the user's lips together and/or keep the user's jaw in a closed position, e.g., such that the lips themselves prevent substantial airflow or breathing through the user's mouth.

In an exemplary embodiment, the membrane 12 may be formed from a non-woven polymeric material that is substantially nonporous, e.g., to prevent airflow through the membrane during normal breathing. Alternatively, the membrane 12 may be formed from a non-woven yet porous material that allows airflow therethrough above a predetermined pressure threshold.

In a further alternative, the membrane 12 may be formed from a woven material or may include filaments or other support materials (not shown) embedded or otherwise attached to a base material. The material may be nonporous or may be porous, e.g., to allow airflow in one or both directions through the membrane. For example, the material may be a mesh that allows limited airflow through the membrane 12 while holding the lips preferentially together.

In addition, the membrane 12 may be formed from compliant material, e.g., for comfort and/or to conform to the shape of the user's mouth and/or surrounding facial features. For example, the membrane 12 may be formed from substantially inelastic material that has sufficient flexibility to conform to the shape of the user's mouth yet support the user's lips and/or jaw. Alternatively, the membrane 12 may be formed from elastic material that is biased to a relaxed profile yet may be resiliently expanded to a stretched profile, e.g., if desired for comfort and/or conformance to the patient's mouth and/or allow some jaw movement.

Further alternatively or in addition, the membrane 12 may be formed from a breathable material that allows passage of moisture away from the skin.

Further alternatively or in addition, the membrane 12 may have a biased compliance or elasticity. For example, the membrane 12 may be relatively more stretchable or elastic in the horizontal direction between the ends 10a, 10b of the adhesive device 10, e.g., substantially parallel to the part line of the lips, and relatively less stretchable or elastic in the vertical direction between the side edges 10c, 10d of the adhesive device 10, e.g., at a right angle to the part line of the lips.

As shown in FIG. 1B, the adhesive layer 14 may be provided substantially continuously on a first or inner surface 12a of the membrane 12. Alternatively, the adhesive layer 14 may be provided discontinuously on the inner surface 12a. For example, the adhesive layer 14 may be provided around an outer periphery of the inner surface 12a, e.g., in an annular layer such that the adhesive layer 14 may contact the user's skin surrounding the lips while a central region has no adhesive material, e.g., to prevent the adhesive from contacting the user's lips. In further alternatives, other configurations may be provided for the adhesive layer 14, e.g., only on end regions 10a, 10b of the adhesive device 10 and not on a central region, and the like. For example, the adhesive layer 14 may be disposed such that it covers the inner surface 12a approximately one third of the width of the lips on either side and does not cover the middle one third of the width of the lips (e.g., about one third the length of the adhesive device 10 from each end region 10a, 10b and not one third of the length corresponding to the central region).

In an exemplary embodiment, the adhesive layer 14 may be formed from a low tack adhesive that may be adherent to skin, yet is also easily removable without leaving significant residue. The adhesive may be selected to provide low irritation and/or be hypoallergenic to prevent irritation or adverse reaction by the user's skin. In addition or alternatively, the adhesive layer 14 may be able to maintain a substantial bond with the user's skin even if it becomes damp. Alternatively, the adhesive layer 14 may be designed to separate from skin at a predetermined pressure, e.g. in the range that may be generated by forced exhalation. In exemplary embodiments, the adhesive layer 14 may comprise one or more of a silicone adhesive, acrylic adhesive, or other types of adhesive.

As shown in FIG. 1A, the adhesive device 10 may have an elongated shape configured to cover a user's mouth, e.g., having rounded first and second ends 10*a*, 10*b* and substantially straight side edges 10*c*, 10*d* extending between the ends 10*a*, 10*b*. In exemplary embodiments, the adhesive device 10 may have a length between the ends 10*a*, 10*b* of between about five and ten centimeters (5-10 cm), and a width between the side edges 10*c* of between about one and five centimeters (1-5 cm).

Figure 2A:
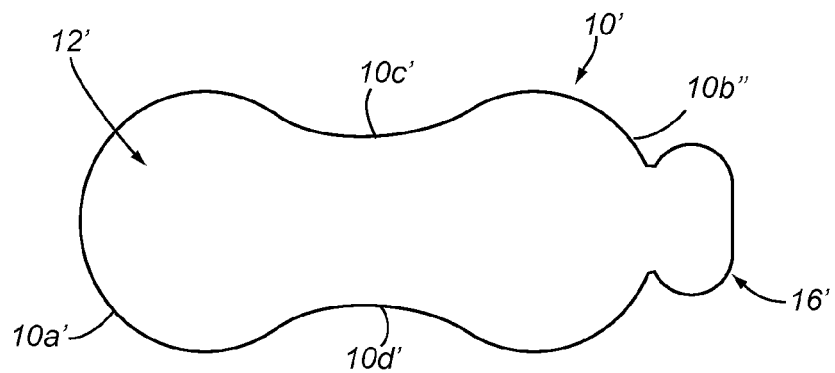
FIGS. 2A-2C are front views of alternative embodiments of an adhesive device for application over a user's mouth.

Alternatively, the adhesive device may have other shapes. For example, as shown in FIG. 2A, the adhesive device 10' may include curvilinear side edges 10*c*,' 10*d*' extending between the ends 10*a*,' 10*b*,' having a relatively narrower width at a central region of the adhesive device 10' and a relatively wider width adjacent the ends 10*a*,' 10*b*.' In this alternative, the adhesive layer (not shown) may be provided on the inner surface of the wider end regions and not the narrower central region.

In addition or alternatively, any of the adhesive devices herein may include a tab, handle, and/or other feature(s) to facilitate removal of the adhesive device 10' after use. For example, as shown in FIG. 2A, a tab 16' may be provided that extends from one end 10*b*' of an adhesive device 10.' The inner surface of the tab 16' may not have an adhesive layer, e.g., such that the tab 16' does not adhere to the user's skin while the adjacent end 10*b*' and other regions of the adhesive device 10' adhere to the user's skin surrounding the user's mouth to provide a desired seal and/or support. Thus, without adhesive on the surfaces of the tab 16,' the tab 16' may be easily grasped and pulled to remove the adhesive device 10.'

Figure 2B:
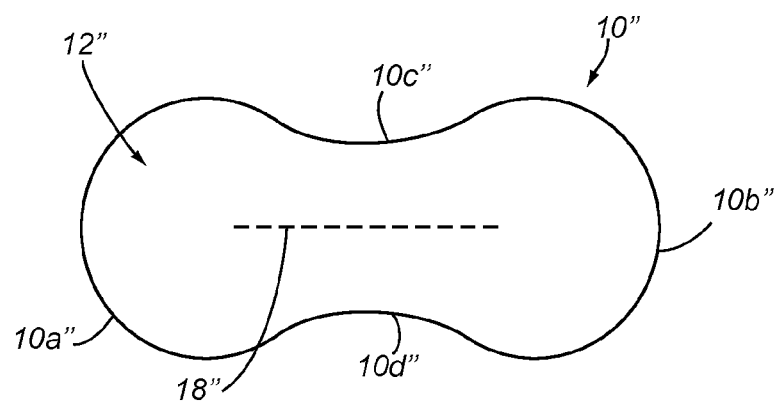

In addition or alternatively, any of the adhesive devices herein may include one or more features for selectively allowing passage of air under predetermined conditions. For example, as shown in FIG. 2B, an adhesive device 10" may be provided that includes one or more weakened regions 18" in the membrane 12." As shown, the weakened regions 18" may include a plurality of indentations or thinned regions that extend partially through the membrane 12," i.e., partially between the inner and outer surfaces. Alternatively, the weakened regions 18" may include perforations extending entirely through the membrane 12." In an exemplary embodiment, the weakened regions 18" may be aligned spaced apart from one another in a line extending at least partially between the ends 10*a*," 10*b*" of the adhesive device 10," as shown in FIG. 2B. Alternatively, a plurality of separate weakened regions may be provided (not shown), e.g., that are spaced apart from one another between the ends of the adhesive device such that each region may selectively tear, separate, or otherwise open to provide individual openings through the adhesive device.

For example, the membrane 12" of the adhesive device 10" may remain intact with the weakened regions 18" sealed until a predetermined pressure threshold is exceeded, whereupon the weakened regions 18" may tear, separate, or otherwise open to allow airflow. For example, the weakened regions 18" may be configured to separate when a deep inspiration above a predetermined pressure threshold is generated by the user, or when a forced exhalation occurs that is above the predetermined pressure threshold (e.g., greater than the positive pressures typically encountered using PAP devices). In addition or alternatively, the weakened regions 18" may be configured to open when a predetermined force threshold is applied between the side edges 10*c*," 10*d*" of the adhesive device 10," e.g., if the user tries to forcibly separate their lips or otherwise open their mouth. In a further alternative, the adhesive layer itself may have predetermined adhesive strength such that the adhesive may separate from the user's skin under such predetermined conditions.

Figure 2C:
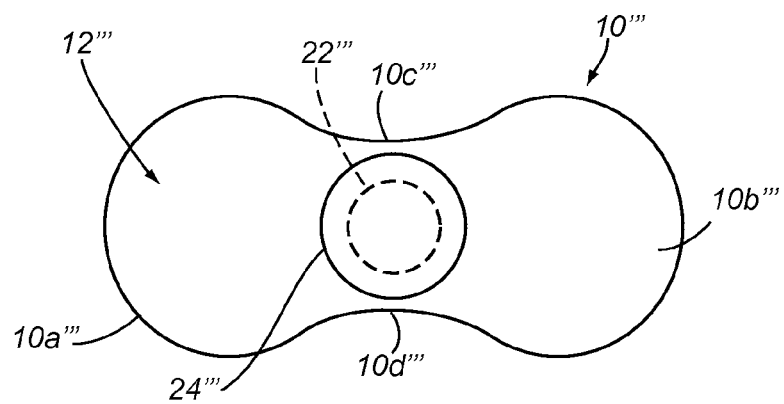

Turning to FIG. 2C, another embodiment of an adhesive device 10''' is shown that includes a membrane 12''' and an adhesive layer (not shown) similar to other embodiments, except that the membrane 12''' includes one or more openings (one opening 22''' shown) therethrough, and a detachable patch 24''' over the opening 22''' (or over each opening if multiple openings are provided). For example, the material of the membrane 12''' may be sufficiently strong to resist tearing or other separation during normal use. The patch 24''' may be formed from a film or other material, e.g., similar to the membrane 12''' or a different material that may be attached to the membrane 12''' over the opening 22.'''

The patch 24''' and/or the membrane 12''' may include adhesive to detachably attach the patch 24''' to the outer surface of the membrane 12''' over the opening 22.''' For example, a continuous layer of adhesive (not shown) may be provided around the perimeter of the patch 24''' and/or around the opening 22''' such that the patch 24''' may be attached to the membrane 12''' to substantially seal the opening 22" from airflow. Alternatively, if desired, the layer of adhesive may be discontinuous (also not shown), e.g., to allow limited flow of air around the patch 24''' into and/or out of the opening 22.''' In addition, the adhesive may be selected such that the adhesive may fail if a predetermined pressure threshold occurs across the opening 22,''' e.g., to cause the patch 24''' to at least partially separate from the membrane 12''' and allow airflow through the opening 22.'''

Turning to FIGS. 3A and 3B, another exemplary embodiment of an adhesive device 110 is shown that includes a one-way valve or flow limiting/prevention device that selectively allows airflow through the adhesive device under predetermined conditions. For example, a one-way valve 126 may be incorporated into the membrane 112 that allows air to flow freely into the user's mouth (i.e., from the outer surface 112*b* through the inner surface 112*a*), or that opens only when a predetermined pressure threshold is exceeded to allow airflow. Alternatively, the one-way valve 126 may allow airflow from the user's mouth (i.e., from the inner surface 112*a* through the outer surface 112*b*) freely or when a predetermined pressure threshold is exceeded. In a further alternative, the one-way valve 126 may allow limited airflow into or out of the user's mouth below a predetermined pressure threshold and increased airflow into or out of the user's mouth above the predetermined pressure threshold.

In the embodiment shown, the adhesive device 110 includes a membrane 112 including an opening 122 therethrough, e.g., in a central region thereof, and an adhesive layer 114 around a periphery of the inner surface 112*a* of the membrane 112. In addition, a flap 126 is integrally formed with or attached to the membrane 112, e.g., such that the flap 126 covers the opening 122.

In one embodiment, the flap 126 may be a separate flexible membrane or film, e.g., formed from similar or compatible materials with the membrane 112, with one edge of the flap 126*a* attached to the inner surface 112*a* of the membrane 112 and an opposite, e.g., curved, edge 126*b* that remains free. Alternatively, the curved edges 126*b* may be detachably attached to the inner surface 112*a* of the membrane 112, e.g., using an adhesive that separates at a predetermined pressure threshold, similar to the patch 24''' of the adhesive device 10''' shown in FIG. 2C.

In another embodiment, the membrane 112 may include multiple layers (not shown), e.g., a first or outer layer that includes the opening 122 and a second or inner layer that includes the flap 126, e.g., by simply cutting or otherwise separating the free edge 126b from the rest of the second layer. The layers may be attached together, e.g., substantially permanently, by one or more of bonding with adhesive, fusing, sonic welding, and the like, except that the area of the flap 126 such that the flap 126 is free to move away from and towards the opening 122.

Thus, during use, the adhesive device 110 may be applied to a user's face, e.g., around the user's mouth similar to the embodiment shown in FIG. 1A such that the flap 126 is disposed adjacent, e.g., against, the user's lips. For example, a cover sheet (not shown) provided over the adhesive layer 114 may be removed, and the adhesive layer 114 may be applied to the user's skin surrounding the mouth, e.g., after the user has pressed their lips together and/or closed his/her mouth/jaw. With the lips pressed together, substantial airflow through the adhesive device 110 may be prevented since the adhesive device 110 may support the lips and/or jaw, e.g., to hold the lips together. Thus, the user may be encouraged and/or limited to breathe nasally rather than through their mouth.

However, if the user's lips separate at all, the flap 126 may prevent airflow out of the user's mouth, e.g., since any positive pressure within the user's mouth applied to the adhesive device 110 may force the flap 126 against the inner surface of the membrane 112 around the opening 122. If a negative pressure is created within the user's mouth that is applied to the adhesive device 110, the pressure may cause the flap 126 to move inwardly away from the opening 122, thereby allowing airflow through the opening 122, e.g., into the user's mouth. Alternatively, the flap 126 may be detachably attached to the membrane 112 such that a predetermined pressure threshold is required, e.g., a particular strong inhalation by the user, to cause the flap 126 to at least partially separate and open the opening 122.

Optionally, any of the adhesive devices herein may be designed to augment sealing of the lips, e.g. by encouraging pursing of the lips or involution of the lips of the user. For example, the user may be instructed to purse their lips before applying the adhesive device, e.g., such that the adhesive device supports and/or holds the lips in the pursed, involuted, or other position, which may enhance sealing and/or undesired airflow through the user's lips.

The adhesive devices herein may be of particular use in conjunction with positive airway pressure, for example, as used to treat sleep apnea. In this setting, mouth leaks can be both bothersome to the patient and decrease efficacy of the treatment. Current methods for preventing mouth breathing are cumbersome and sometimes ineffective. For example, with the adhesive device 110 shown in FIGS. 3A and 3B, positive pressure within the user's mouth, e.g., generated by a PAP nasal device placed over the user's nose, may cause the flap 126 to be pressed against the inner surface 112a of the membrane 112 to substantially seal the opening 122 and prevent the pressure from the PAP device from leaking out of the users mouth between their lips.

In addition, the adhesive device 110 may hold the lips pressed together and/or hold the jaw closed to prevent mouth breathing. Thus, the user may breathe through their nose, e.g., assisted by the PAP device. In this manner, the adhesive device 110 over the mouth in conjunction with nasal positive pressure may prevent mouth breathing, thereby maintaining therapeutic elevated airway pressure, preventing drying of the mouth, bothersome leaks, and/or other problems often encountered using PAP devices.

In addition, the adhesive devices herein may hold the mouth closed without a PAP device to encourage nasal breathing, thereby reducing snoring, mouth dryness, and/or other problems encountered when the user otherwise breathes through their mouth.

Turning to FIGS. 4A and 4B, another embodiment of an adhesive device 210 is shown that includes a lip closing element 212, a mouth cover 220 for securing the lip closing element 212 relative to a user's mouth, and a flap 226. Generally, the mouth cover 220 is an annular member sized and/or shaped to be applied around a user's mouth, e.g., against the skin adjacent the user's lips. Similar to other embodiments herein, the mouth cover 220 includes an adhesive layer (not shown), e.g., on an inner surface 220a of the mouth cover 220, for application against the user's skin to secure the adhesive device 210 over the user's mouth.

For example, the mouth cover may be a double-sided adhesive membrane that includes a central or base layer including an inner surface 220a and an opposite outer surface (not shown), both of which include an adhesive layer. The first or inner adhesive layer on the inner surface 220a may provide a low tack and/or low residue for securing the adhesive device 210 around a user's mouth, similar to other embodiments herein. The second or outer adhesive layer (not shown) on the outer surface may substantially permanently attach other components of the adhesive device 210 to the mouth cover 220. The base layer of the mouth cover 220 may be formed from materials similar to other membranes herein, e.g., providing desired flexibility and/or conformance to a user's face.

Similar to other embodiments herein, the mouth cover 220 may include one or more tabs (two tabs 216 shown on opposite ends of the mouth cover 220), which do not include any adhesive on the inner or skin contact surface (or other surfaces). Thus, the tab(s) 216 may be easily pulled and/or otherwise separated from the user's skin to facilitate removing the adhesive device 210, as described elsewhere herein.

With additional reference to FIG. 4C, the lip closing element 212 may be a flexible membrane, e.g., formed from materials similar to any of the other embodiments herein, that may be attached to the outer surface of the mouth cover 220. For example, an outer periphery of the inner surface 212a of the lip closing element 212 may be attached to the adhesive layer on the outer surface of the mouth cover 220 to substantially permanently attach them together. In an exemplary embodiment, the lip closing element 212 may be formed from urethane, PEBAX, silicone, or other elastomeric material. Further alternatively, the lip closing element 212 may be formed from a mesh, multiple bands, and/or other substantially air permeable material.

Optionally, as shown, the lip closing element 212 may include one or more openings therethrough, e.g., three openings 222 as shown, to allow the user to breathe, speak, and/or perform other actions when the adhesive device 210 is secured over the user's mouth. For example, the lip closing element 212 may be a membrane formed from elastic material with the openings 222 biased to a relaxed or relatively small area configuration, yet resiliently deflectable to open the openings 222 to an expanded or relatively large area configuration. The support regions between the openings 222 may have sufficient structural integrity and/or elasticity to bias the openings to the small area configuration, yet allow the lip closing element 212 to be stretched elastically to expand the openings. If the lip closing element 212 is formed from relatively low Durometer elastomeric material, the material may need to be thicker or the width of the support elements between the openings wider (e.g., by making the openings 222 smaller or further apart from one another) to provide the same lip closing force as a lip closing element constructed with a relatively higher Durometer material.

Thus, with the adhesive device 210 secured over a user's mouth, the openings 222 may be biased to the small area configuration to minimize airflow through the openings 222. In the small area configuration, the openings 222 may be substantially circular or may be elliptical, e.g., having the major axis parallel to the length of the adhesive device 210 and the minor axis parallel to the width of the adhesive device 210. The user may force their lips apart, thereby stretching the lip closing element 212 and/or otherwise expanding the openings 222, which may facilitate speaking, breathing, removing spittle or other material, and/or taking other actions.

Optionally, the adhesive device 210 may also include one or more flaps or other valve(s) 226 attached to the mouth cover 220 and/or lip closing element 212. For example, as best seen in FIG. 4B, a flap 226 may be positioned between the mouth cover 220 and lip closing element 212 and secured therebetween, e.g., by tabs 227. With the tabs 227 secured to the mouth cover 220 and/or lip closing element 212, the flap 226 may move towards the lip closing element 212, e.g., to close and/or seal the openings 222, and/or away from the lip closing element 212, e.g., into the opening through the mouth cover 220 to allow airflow through the openings 222. Further, at least some of the one or more flaps or other valves may be substantially aligned with the part line of the lips. Further if the one or more flaps or other valves are constructed to open inwardly, they may be positioned to open into the space created between the lips when the lips are at least partially opened.

In exemplary embodiments, the flap 226 may be formed from relatively thin, strong, flexible material, such as urethane, PET, PEBAX, and the like. The flap 226 may be formed from inelastic material such that the flap 226 does not stretch but simply moves relative to the lip closing element 212.

For example, if the user separates their lips, the flap 226 may still initially cover the openings 222 in the lip closing element 212. Thus, in this position, positive pressure across the adhesive device 210 (i.e., relatively higher pressure inside the user's mouth than outside) causes the flap 226 to press against the lip closing element 212, sealing the openings. The user may be able to inhale to generate a negative pressure, thereby directing the flap 226 away from the lip closing element 212 and allowing the user to inhale through the openings 222.

If the lip closing element 212 (and mouth cover 220) are sufficiently elastic, the user may be able to open their lips further, i.e., until the flap 226 no longer covers the openings 222. In this further expanded configuration, since the openings 222 are fully open, the user may be able to inhale and exhale, as desired. When the user relaxes their lips and/or mouth, the lip closing element 212 may resiliently close or return towards the relaxed configuration, thereby covering the openings 222 once again with the flap 226.

Optionally, the adhesive device 210 may include one or more additional features, as desired. For example, safety scores (e.g., similar to the weakened regions described elsewhere herein), breakable elements, stretchable elements, and the like (not shown) may be provided on the mouth cover 220 and/or the lip closing element 212. In addition or alternatively, the flap 226 may be tuned to allow for programmed rupture at a given exhalation pressure, with forced opening of the mouth, and the like, e.g., causing the flap material 226 to tear or separate from the tabs 227. The pressure of normal breathing (even with PAP) is much lower than the pressure an individual can readily produce when needed/desired such as in an emergent situation (e.g., if the user needs to vomit, and the like). Thus, the adhesive device 210 (and the other embodiments herein) may be readily fabricated to provide a device that is both safe (e.g., that may break away when needed) and effective (i.e., stay together) under normal use to maintain the user's mouth closed and/or sealed.

During use, the adhesive device 210 may be applied over a user's mouth by attaching the mouth cover 220 to skin surrounding the user's mouth. For example, if a cover sheet (not shown) is provided over the adhesive on the inner surface 220a, the cover sheet may be removed to expose the adhesive, and then the inner surface 220a may be pressed against the skin surrounding the user's mouth. The user may purse their lips and/or otherwise close or position their lips and mouth such that the lip closing element 212 is positioned adjacent the user's lips with the lip closing element 212 in its relaxed or small area configuration.

If the adhesive device 210 includes the flap 226, the flap 226 may be positioned against the user's lips with the lip closing element 212 outside and against the flap 226. Under normal use, the user's lips are held closed to prevent breathing in or out through the mouth, e.g., to enhance PAP use, nasal breathing, and/or prevent snoring and/or other undesired mouth breathing.

However, for some users, during the accommodation period when the adhesive device 210 is first applied over the user's mouth, the user may feel a sense of anxiety about the ability to get enough air through their nose. With minimal opening of the lips, air may be easily inspired through the openings 222, as described above, but prevented from escaping, e.g., to encourage good breathing protocol. Further, if needed or desired, exhalation through the mouth may still be readily accomplished if the lips are further opened causing the openings 222 to extend beyond the flap 226, also as explained above. After use, e.g., after sleeping, the adhesive device 210 may be removed, e.g., by pulling one or both tabs 216 to remove the mouth cover 220 from the user's skin.

Turning to FIGS. 5A and 5B, another embodiment of an adhesive device 310 is shown that includes a membrane 312 and an adhesive layer (not shown), generally similar to other embodiments herein. In addition, the adhesive device 310 includes one or more flaps 326 (e.g., three as shown) that may be configured to allow flow in only one direction across the membrane 312, similar to other embodiments herein. In the embodiment shown, the flaps 326 may be formed in a second layer of material, e.g., similar to or compatible with the material of the membrane 312, attached to either side of the membrane 312. For example, the membrane 312 may include a shape similar to any of the embodiments herein with an opening 322 formed therethrough. The flaps 326 may be cut or otherwise formed in a film or membrane having a periphery 327 that is attached to the membrane 312 around the opening 322. The flaps may be configured to move away from and/or towards the opening 322 or otherwise open when a negative pressure is generated across the membrane 312, e.g., when a user inhales, but otherwise close when a positive pressure is generated, e.g., due to PAP use or ordinary exhalation.

In an alternative embodiment shown in FIGS. 6A and 6B, the adhesive device 310' may be formed from three layers of material. For example, the first layer may be a membrane 312' including the opening 322,' and the second layer may include the flaps 326.' In addition, in this embodiment, a third layer 328' is provided that allows the flaps 326' to substantially open in only one direction. For example, the third layer 328' may be a nonporous layer of material, a mesh, a series of separate bands (not shown), and the like, similar to other embodiments herein. The third layer 328' may be substantially inelastic, stretchable in one direction, or substantially elastic. Similar to other embodiments, when a positive pressure is generated across the membrane 312,' the flaps 326' may be at least partially prevented from opening by the third layer 328,' and may thereby create a substantial expiratory seal, yet may open away from the third layer 328' when a negative pressure is generated. The adhesive devices 310, 310' may otherwise be used similar to other embodiments herein.

With reference to FIGS. 6A and 6B, further alternatively, the second layer may be omitted and the flaps 326' prime may be formed in the first layer 312.' In this case, the adhesive layer may be generally omitted from the area of the flaps 326.' The third layer 328,' as previously described, may at least partially prevent the flaps 326' from opening and thereby create a substantial seal when a pressure differential is applied so as to direct the flaps toward the third layer 328,' e.g., due to PAP use or ordinary exhalation.

Generally, the adhesive devices herein may be provided as a single-use device, e.g., that may be applied over a user's mouth for a single night's sleep. Thus, the adhesive device may be applied before sleep, e.g., before or after placing a PAP nasal cover over the user's nose, and then removed and discarded after waking. Alternatively, the adhesive devices may be constructed and adhesive selected to permit removal and replacement each time the user sleeps, and/or to allow other reuse.

The adhesive devices may be easily fabricated using large volume manufacturing, e.g., by providing the components as simple sheets or spooled reels of films that may be used to make multiple devices simultaneously and/or sequentially. The individual layers may be laid up and attached together and then separated into individual devices, similar to known manufacturing methods. For example, a first web may be provided for the mouth covers, e.g., having adhesive on both sides. A first side may provide an adhesive layer for later adherence to a user's mouth of an individual device, and a second side may be used to adhere to the lip closing elements and relief hole web. The optional flap may be pinned in place between the mouth cover web and the lip closing element and relief hole web. Tabs may also be included on the mouth cover web, both for easy adhesive backing removal (done by individual consumer at time of application) and/or easy of removal from a user's mouth after use is complete. Safety scores may be cut or otherwise formed into the web(s) at the same time their profile is cut from the web.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods do not rely on the particular order of steps set forth herein, the methods should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:
1. A device for improving breathing, comprising:
a mouth cover comprising an annular member defining a central open region therethrough and including a first surface comprising adhesive thereon for detachably attaching the mouth cover to skin of a user surrounding the user's mouth;
a lip closing element comprising an elastic membrane attached to a second surface of the mouth cover opposite the first surface and extending across the central open region and including one or more openings therethrough; and
a one-way valve attached to the mouth cover for selectively sealing the one or more openings when a positive pressure within a user's mouth is generated between the first and second surfaces, and opening the one or more openings when a user inhales to generate a negative pressure between the first and second surfaces,
wherein the lip closing element is stretchable to allow the user to open the user's mouth until the one-way valve no longer covers the one or more openings to allow the user to inhale and exhale, and wherein the lip closing element is biased to resiliently close, thereby covering the one or more openings with the one-way valve when the user relaxes the user's mouth.

2. The device of claim 1, wherein the membrane has an elasticity greater than the material of the mouth cover.

3. The device of claim 1, wherein the one-way valve comprises one or more flap valves attached between the mouth cover and the lip closing element.

4. The device of claim 1, wherein the membrane of the lip closing element is formed from elastic material such that the one or more openings are biased to a relaxed configuration, yet are resiliently deflectable to open the openings to an expanded configuration having a relatively large area compared to the relaxed configuration.

5. The device of claim 1, wherein the mouth cover comprises one or more tabs with non-adhesive surfaces to facilitate removal of the mouth cover from over the user's mouth.

6. A method for improving breathing of a PAP user, comprising:
placing a nasal mask for a PAP device over a user's nose;
applying an adhesive layer of a membrane over the user's mouth to prevent breathing through the user's mouth, the membrane comprising a one-way valve therein covering one or more openings;
activating the PAP device, wherein activating the PAP device creates a positive pressure within the user's mouth that substantially seals the one-way valve to prevent flow through the one or more openings; and
inhaling to generate a predetermined negative pressure within the user's mouth, thereby causing the one-way valve to open and allow air to pass through the one or more openings into the user's mouth, wherein the membrane is stretchable to allow the user to open the mouth until the one-way valve no longer covers the one or more openings to allow the user to inhale and exhale, and wherein the membrane is biased to resiliently close, thereby covering the one or more openings with the one-way valve when the user relaxes the mouth.

7. A method for improving nasal breathing, comprising:
applying an adhesive layer of a membrane over a user's mouth with the user's lips pressed together, the membrane comprising a one-way valve therein covering one or more openings, and wherein positive pressure within the user's mouth substantially seals the one-way valve to prevent flow through the one or more openings;
sleeping with the membrane over the user's mouth to inhibit breathing through the user's mouth; and
inhaling to generate a predetermined negative pressure within the user's mouth, thereby causing the one-way valve to open and allow air to pass through the one or more openings into the user's mouth,
wherein the membrane is stretchable to allow the user to open the mouth until the one-way valve no longer covers the one or more openings to allow the user to inhale and exhale, and wherein the membrane is biased to resiliently close, thereby covering the one or more openings with the one-way valve when the user relaxes the mouth.

8. The method of claim 7, wherein the membrane comprises one or more weakened regions therein, the method further comprising:
one of inhaling or exhaling to generate a pressure across the membrane greater than a predetermined pressure threshold, thereby causing the one or more weakened regions to tear to allow breathing through the user's mouth.

9. The method of claim 7, wherein the membrane comprises one or more weakened regions therein, the method further comprising:
forcibly separating the user's lips to cause the one or more weakened regions to separate and allow breathing through the user's mouth.

* * * * *